United States Patent [19]

Nygren et al.

[11] Patent Number: 4,558,012

[45] Date of Patent: Dec. 10, 1985

[54] METHOD AND MEMBER FOR DETECTING AND/OR MEASURING THE CONCENTRATION OF A CHEMICAL SUBSTANCE

[75] Inventors: B. Hakan Nygren, Billdal; E. Torbjörn Sandström, Mölndal; Johan E. Stenberg; Lars B. Stiblert, both of Gothenburg, all of Sweden

[73] Assignee: Sagax Instrument AB, Taby, Sweden

[21] Appl. No.: 488,794

[22] Filed: Apr. 26, 1983

[30] Foreign Application Priority Data

Apr. 26, 1982 [DE] Fed. Rep. of Germany ....... 3215484

[51] Int. Cl.$^4$ ..................... G01N 33/54; G01N 21/54
[52] U.S. Cl. ..................................... 436/501; 422/57; 435/7; 436/518; 436/527
[58] Field of Search ................. 435/7; 436/518, 514, 436/515, 516, 527; 422/57, 56, 58; 427/255.7, 2; 428/331, 391, 428, 429; 204/180 R, 180 G, 299 R

[56] References Cited

U.S. PATENT DOCUMENTS 3,926,564 12/1975 Giaever ................................ 422/57
3,979,184 9/1976 Giaever ................................ 422/57
4,181,501 1/1980 Keese et al. ......................... 436/514

FOREIGN PATENT DOCUMENTS 2416047 10/1975 Fed. Rep. of Germany ........ 422/56
2512730 10/1975 Fed. Rep. of Germany .

OTHER PUBLICATIONS

Vroman, Effect of Hydrophobic Surfaces Upon Blood Coagulation Thromb. Diath. Haemorrhag., vol. 10, pp. 455–493, (1964).
Nygrer and Stenberg, Electrophoresis of Ligands Over a Surface Coated with a Binding Receptor, FEBS Letters, vol. 135, No. 1, pp. 73–76, (1981).
Giaever and Laffin, Visual Detection of Hepatitis B Antigen, Proc. Nat. Acad. Sci., U.S.A., vol. 71, pp. 4533–4535, (1974).
Stenberg, Sandström, and Stiblert, A New Ellipsometric Method for Measurement on Surfaces and Surface Layers, Materials Science and Engineering, vol. 42, pp. 65–69, (1980).
Blodgett and Langmuir, Built-Up Films of Barium Stearate and their Optical Properties, Pysical Review, vol. 51, pp. 968–978, (1937).
Giaever, The Antibody–Antigen Reaction: A Visual Observation, The Journal of Immunology (J. Immu.), vol. 110, No. 5, pp. 1424–1426, (1973).
Laffin, Visual Detection of Hepatitis B Surface Antigen and Antibody, Biochemical Appl'n of Immobilized Enzymes and Protein (Ed. by Chang), vol. 2, pp. 147–162.
Laurell, Quantative Estimation of Proteins by Electrophoresis in Agarose Gel Containing Antibodies, Analytical Biochemistry, vol. 15, pp. 45–52, (1966).
Elwing and Nygren, Diffusion in Gel-Enzyme Linked Immunosorbent Assay (Dig-Elisa): A Simple Method for Quantitation of Class-Specific Antibodies, J. Immu. Method, vol. 31, pp. 101–107, (1979).
Adams, Klings, Fischer, and Vroman, Three Simple Ways to Detect Antibody Antigen Complex on Flat Surfaces, J. Immu. Method, vol. 3, pp. 227–232, (1973).
Elwing and Stenberg, Biospecific Bimolecular Binding Reactions-A New Ellipsometric Method for their Detection, Quantification and Characterization, J. Immu. Method, vol. 44, pp. 343–349, (1981).

*Primary Examiner*—Sidney Marantz
*Assistant Examiner*—Cynthia Lee Foulke
*Attorney, Agent, or Firm*—Fleit, Jacobson, Cohn & Price

[57] ABSTRACT

A member for detecting and/or measuring the level of concentration of a chemical substance in a medium comprises a non-metal substrate bearing a dielectric layer. A detection reactant which is capable of reacting with the substance to be detected is put on the dielectric layer and the assembly is put into the medium to be investigated, whereupon an optically detectable layer of the substance to be detected is formed on the detection reactant. The substrate is light-absorbing and one or more further dielectric layers is or are disposed between the substrate and the first-mentioned dielectric layer thereon, the thickness of the further dielectric layer or layers being such that the overall assembly comprising all the dielectric layers, the layer of detection reactant thereon and the layer of substance to be detected, is reflection-reducing in respect of non-monochromatic light which is reflected at the surface of the substrate on which the array of layers is disposed, in the wavelength range of from 525 to 600 nm.

28 Claims, 5 Drawing Figures

METHOD AND MEMBER FOR DETECTING AND/OR MEASURING THE CONCENTRATION OF A CHEMICAL SUBSTANCE

BACKGROUND OF THE INVENTION

In regard to biochemical and immunological investigations, there is a great need for detecting and measuring thin organic surface layers, in particular surface layers of that kind which have refractive indices of about 1.50 and which are of thicknesses in the range of from 1 to 10 nm. Such investigations are of particular interest in connection with toxin-receptor, enzyme-substrate or antigen-antibody reactions. It is known that an antigen-antibody reaction, that is to say, binding an antigen to its specific antibody, takes place even when one of the two reactants is bound to a surface of a substrate or a slide. It is therefore possible to bind a protein from a microorganism to a surface of a slide and immerse the slide in blood serum from a person. If that person is injected with a microorganism and the blood serum contains antibodies against the proteins of the microorganism, such antibodies will be bound to the protein which is present on the immersed surface of the slide if that protein is of the same type as the proteins of the microorganism. In that way, an organic layer is grown on the immersed surface. In the same way, it is obviously also possible for an antibody against a given protein to be bound to the immersed surface and used to detect the protein in the solution. Such investigation procedures have become increasingly important in recent years, particularly because monoclonal antibodies against a wide range of proteins can be produced by hybridoma techniques. An advantage of surface reactions, as compared to reactions in a liquid phase, is that there is only a low level of consumption of reagents.

However, the use of antibodies and antigens which are immobilised on surfaces or bound to surfaces in immunological investigations is hampered by the lack of simple and sensitive methods for measuring the thickness of the organic films, in the nm-range. An ellipsometer is used for that purpose in laboratory procedures. However, that is relatively expensive and can only be used by a skilled operator. Simplified investigation techniques which are based for example on the change in wettability, the scattering of light from metal particles and the sticking of colloidal particles have not been successful under practical conditions. Such simplified methods make use of the difference between a restricted area of the surface and the area around it. In such an operation, the restricted part of the surface is coated with an antigen or antibody, while the surrounding area is coated with another organic substance, in the same thickness. If proteins are bound in the restricted part of the surface, and not to the surface therearound, the thickness of the layer in the restricted part of the surface is greater than in the surrounding area. That gives different physical properties.

Antigen-antibody reactions and dielectric layers on reflecting carriers or substrates were the subject of the investigation a long time ago by Blodgett and Langmuir (Physical Review, volume 51, June 1937, pages 964 to 978).

Such investigations show that thin organic films on polished chromium surfaces can be observed if they are not applied directly to the naked surface but are applied to a barium stearate film which is formed on the chromium surface. Strong interference phenomena cannot be achieved, because the refractive indices are not of the optimum values, with a perpendicular angle of incidence. With angles of incidence, the interference phenomenon is greater, but in that case there are differences in the two polarisation states. It is therefore only possible to achieve substantial suppression of an individual wavelength, by simultaneously using a polarising means. When the sample is viewed through a polarising means, and by measuring the angle of incidence at minimum intensity, it is possible to determine the thickness of monomolecular films, in accordance with Blodgett and Langmuir, with a relatively high degree of accuracy, and thus detect a binding reaction between antigens and antibodies on surfaces. Immunological reactions have been investigated in this case, using a rudimentary ellipsometry process.

The use of substantial interference phenomena of tantalum oxide on tantalum has also been the subject of publication by Vroman (Thromb. Diath, Haemorrhag, volume 10, pages 455 to 493 (1964), in particular page 463).

Anodized tantalum plates with a dark brown colouring change towards violet if they are coated with a monomolecular protein layer. The oxide forms an anti-reflection coating on the metal and the plate has a brown appearance if the reflection of blue and green light is suppressed to a greater extent than the reflection of longer wavelengths. When a thin layer of protein is formed on the surface, the thickness of the transparent layer increases and the reflection minimum moves towards longer wavelengths. The reflected light therefore contains more blue and violet components, if a biological layer, for example a layer of protein, is present.

The same properties as were found by Vroman were also attained by Giever and Laffin, when a gold-indium alloy was applied to a glass slide and gradually oxidized so as to produce a brownish colour (The Journal of Immunology, volume 110, No 5, May 1973, pages 1424 to 1426; Biomedical Applications of Immobilized Enzymes and Proteins, volume 2, pages 147 to 162).

The last three known processes mentioned made use of the effect that thin biological layers, for example protein layers, which are applied to dielectric layers of a given thickness, alter the interference phenomena of the original dielectric layer. The known processes involve using metals which, when they are used as substrates, require thereon films which have a high refractive index if good interference properties are to be achieved, although a low level of optical detection sensitivity is tolerated. There is also the danger that the reactants might be affected by contact with the metal or metal oxides. That is an undesirable situation, particularly when the substance to be detected is present in the solutions in only low levels of concentration, and long incubation periods are required. Metal substrates, or metal oxide layers disposed thereon, also have indefinite surface properties as the surface energy and the surface density of the binding locations change and therefore the binding effect or the adsorption of organic molecules cannot be controlled with sufficient accuracy in that respect.

U.S. Pat. Nos. 3,926,564 and 3,979,184 also disclose metal systems for rendering thin surface layers visible. In U.S. Pat. No. 3,979,184, a dielectric layer is disposed between a metal substrate and a semi-transparent metal layer, while U.S. Pat. No. 3,926,564 provides that an oxide is formed on a noble metal alloy having an oxidizable component. Those processes also involve metal systems in which, as already mentioned above, a low level of optical detection sensitivity is tolerated.

It is also known (see Laurell, C.B. 'Quantitative estimation of protein by electrophoresis in agarose gel containing antibodies', Anal. Biochem. 15: 45, 1966), for the substance to be detected, or the amount thereof, to be allowed to spread by electrophoresis in a gel which contains a homogeneously distributed concentration of a reactant which reacts with the substance to be detected. The two reactants react by precipitation in the gel, and the reaction region is rendered visible, the reaction region being limited to the area in which the reactant for the substance to be detected is contained from the outset. That system provides quick and accurate detection. However, that detection method is subject to the restriction that the reactant which is used for the detection operation should not migrate in the electrical field, thereby giving rise to limitations in regard to the electrophoresis conditions such as for example the pH-value, the gel quality and the polarity involved. In addition, that method is restricted to those reactions which result in a precipitation effect.

In another known method (see Elwing, H. and Nygren, H. 'Diffusion in gel-enzyme linked immunosorbent assay (DIG-ELILSA): A simple method for quantification of class-specific antibodies', J. Immun. Methods, 31:101, 1979), the substances to be detected spread out by diffusion in a gel which is disposed above a surface provided with a thin layer of a reactant for detecting the substance in question. After a certain period of time, the gel is removed and the reaction region on the surface is rendered visible. The size of the reaction region is measured and constitutes a measurement in respect of the amount of the substance to be detected, which is diffused over the surface. The step of rendering the reaction product at the surface visible can be performed by secondary reactions such as by incubation with an isotope or enzyme-labelled antibodies directed against the reaction product bound after the diffusion process.

It is also possible to perform the detection operation by a water condensation process (Adams, A.L., Klings, M., Fischer, G.C. and Vroman, L., 'Three simple ways to detect antibody antigen complex on flat surfaces', J. Immun. Methods, 3:227, 1973). In addition, the reaction products may be rendered visible by direct optical analysis of the primary reaction product, by ellipsometry (Elwing, H. and Stenberg, M. 'Biospecific bimolecular binding reactions—a new ellipsometric method for their detection, quantification and characterization', J. Immun. Methods, 44:343, 1981) or by light interference on thin layers (Adams, A.L., Klings, M., Fischer, G.C. and Vroman, L., 'Three simple ways to detect antibody antigen complex on flat surfaces', J. Immun. Methods, 3:227, 1973). In rendering the reaction product visible, the advantage of a high level of sensitivity is attained by means of intensification reactions such as for example by using enzyme-labelled antibodies, while the optical detection methods provide direct detection of the primary reaction product. In addition, the optical detection methods do not use any reactant other than the reactant required for detection purposes.

In the diffusion method in which a surface is coated with a reactant for detecting a substance, there is the advantage, in comparison with the passive or active transport reaction of a reactant which is distributed in a gel, that it is also possible to investigate or detect reactions which do not result in a precipitation effect. In order to immobilise the reactant on the surface, there are a number of possible ways of binding the molecules of the reactant which is to be used for detecting the other substance. However, the diffusion methods involve a relatively long diffusion time. However, with the method disclosed in FEBS Letters, volume 135, No 1, November 1961, pages 73 to 76, it is possible to cause the substance to be detected to react with the reactant present on the surface of the substrate, by a binding action, in a relatively short period of time and at low cost. In addition, there are no limitations in regard to the electrophoresis conditions. However, difficulties do arise in regard to simplifying the step of rendering visible the substance to be detected, which is bound on the binding agent present on the surface of the substrate. There is also the danger, when using metal substrates, of undesirable electrochemical reactions, for example the formation of oxides on the substrate surface.

Biomedical methods of detecting organic substances in solutions are also known from German laid-open application (DE-OS) No. 25 12 730 and U.S. Pat. No. 4,181,501. The former specification discloses radial diffusion of the substance to be detected, in a gel, and transportation of that substance by means of electrophoresis in a gel, but the step of detecting such substances is performed by means of metal plates in regard to which, as already referred to above, a relatively low level of sensitivity has to be tolerated.

SUMMARY OF THE INVENTION

An object of the present invention is to provide a method and member for detecting and/or measuring the concentration of a chemical substance, wherein a high degree of optical detection sensitivity can be attained without the chemical detection reaction being hampered by the material used for the member for performing the method.

Another object of the present invention is to provide a method for the detection and quantification of a chemical substance which can be carried out without any instrument and which involves using only inexpensive material.

Still another object of the present invention is to provide a method of detecting and/or measuring the amount or concentration of a chemical substance, which can be used selectively to provide a preliminary or outline indication or to provide an indication of maximum sensitivity.

Yet another object of the present invention is to provide a method of detecting a chemical substance which is simple and reliable in operation and which will provide a high degree of reproducibility.

A further object of the present invention is to provide a member for detecting and/or measuring the level of concentration of a chemical substance, which has both a high degree of sensitivity and a high level of physical ruggedness.

Still a further object of the present invention is to provide a member for detecting and/or measuring the concentration or amount of a chemical substance, by using direct visual means.

Yet a further object of the present invention is to provide such a member which is suitable for industrial production on a large scale so as to be readily available in quantity, while also being low in cost in relation to the total costs involved in performing such testing operations.

In accordance with the present invention, these and other objects are achieved by a method of detecting and/or measuring the concentration or quantity of a biochemically reactive substance, wherein the substance to be detected is reacted with a detection reactant or counter reactant disposed on a member comprising a plurality of layers, in a medium such as water, gel or blood serum. The substance to be detected is thus formed as an optically detectable layer on the member. The member comprises a non-metallic substrate and a first dielectric layer of $SiO_2$ thereon. Disposed between the substrate and the first dielectric layer is or are one or more further dielectric layers, of such a thickness and with such a refractive index that, when a layer of detection reactant which is reactive with the substance to be detected, and a layer of said substance, are applied to the member comprising the substrate and the dielectric layers, the overall array of such layers is adapted to reduce reflection in respect of non-monochromatic or white light which is reflected at the surface of the substrate on which the array of layers is disposed, in the wavelength range of 525 to 600 nm.

The invention also provides therefore a detection member comprising a substrate, a first dielectric $SiO_2$ layer thereon, and one or more further dielectric layers between the substrate and the first dielectric layer, which can be used in carrying out the above-defined method according to the principles of this invention.

The invention makes use of the realisation that the residual light which is reflected by a reflection-reducing or anti-reflection surface, when irradiated with white or non-monochromatic light, can constitute an instrument with a high degree of detection sensitivity, for detecting changes in the properties of the reflection-reducing layer when, as in the case of the present invention, all the surface layers, that is to say, both the dielectric layers and also the layers of biological origin which are formed or produced thereon, form the reflection-reducing layer. In that connection, very slight changes in layer thickness and in particular changes in layer thickness which are in the molecular range can be detected by changes in the colour of the reflected light, by virtue of the production of interference colours. It will be appreciated therefore that a surface layer that adds to the thickness of the dielectric layer will change the interference colour, and with a properly designed such member, a fraction of a nanometer can be detected.

In accordance with an advantageous feature of the invention, the detection member may be of such a configuration that the detection reactant is provided on the surface of the array of layers, only at one or more deferred locations thereon. A preferred arrangement is one in which the reactant occurs on the layer array in an island-like form and is surrounded by a layer of non-active organic substance of the same thickness and optical properties. In that case, both the layer of detection reactant and the layer of non-active organic substance are applied to the dielectrically operative layer in a monomolecular form, a layer of $SiO_2$ preferably being employed as the dielectric layer.

In that connection, use may be made of the fact that an $SiO_2$ surface can be of such a chemical nature that it is possible to achieve good binding properties in relation to various organic molecules. If the silicon member or substrate with the $SiO_2$ surface is introduced into a solution containing a protein, the surface of the layer of dioxide becomes coated with a monomolecular layer of the protein. The coated silicon member or substrate can then be dried and also stored over a prolonged period of time, without losing the protein coating. If the coated member is introduced into another solution, the protein coating can react with substances in that solution, for example antibodies, which are then bound to the protein. The silicon dioxide is inert and does not give off any atoms or groups of atoms which take part in such reactions or which detrimentally affect the proteins. Consequently, the outer surface of silicon dioxide on the coated member has inert properties which however can be put to versatile uses in accordance with the present invention.

A reproducible $SiO_2$ surface can be achieved by cleaning in a mildly oxidizing solution. In that connection, a wide range of reproducible surface properties can be achieved by means of known methods. Functional groups such as amino groups can be covalently bound to the surface by means of commercially available coupling agents, for example organo-silicon compounds. Larger organic molecules such as proteins can be bound to the functional groups in that way. That permits the surface to be coated with a monomolecular covalently bound organic layer, in particular a protein layer. In many cases, the $SiO_2$ surface merely has to be treated with dichlorodimethylsilane, thereby producing a highly hydrophobic surface on which the larger organic molecules such as proteins, which form the layer of detection or counter reactant, can be substantially adsorbed.

The substrate may comprise silicon and may be provided with the anti-reflection coating at the surface on which the $SiO_2$ layer is disposed. In comparison with metal substrates which admittedly have a high degree of reflectivity and thus pleasing appearance and also the possibility of the metal oxides being used as the anti-reflection layer, the substrate according to the present invention has the advantages that it does not react with the solution and therefore no atoms or groups of atoms from the substrate pass into the solution. The biochemical properties are not affected, that being a factor which could result in erroneous results. While metals have wavelength-dependent refractive indices and thus the high reflectivity imposes severe restrictions in regard to the choice of the anti-reflection coating, the dielectric material which is used in accordance with the principles of the present invention has a lower refractive index which is less dependent on wavelength. It has been found that suitable substrates are those comprising glass or plastic material. Such materials are readily obtainable and mechanically strong. They are chemically inert and can be cleaned by chemical agents.

The non-metallic substrate material has a substantially dielectric refractive index in which the imaginary portion is negligibly small relative to the real portion, whereas in the case of the refractive indices of metals, the real portions and the imaginary portions are of the same order of magnitude.

Langmuir and Blodgett (Physical Review, volume 51, June 1937, pages 964 and 978) were in fact also investigating barium stearate on glass, but it was found that the interference phenomena, at inclined angles of incidence, were weaker than on chromium, even when using a polarizer. Although barium stearate on glass is optically related to $SiO_2$ on glass, interference under practical conditions of use is too weak without the dielectric intermediate layers which are used in accordance with the present invention. In addition, barium stearate on the glass substrate does not have the desired surface properties, like the $SiO_2$ layer.

Calculations have shown that an anti-reflection coating comprising a single layer, that is to say, a coating which gives a high degree of suppression of reflection at a particular wavelength near the sensitivity maximum of the eye (that is to say, 570 nm) imparts a high degree of detection sensitivity to the surface layers. For a silicon dioxide layer to ensure good suppression of the reflected light, the substrate must have a refractive index of the order of magnitude of 2.13. Glasses which have good substrate properties in accordance with the present invention have refractive indices in the range of from 1.50 to 1.80, while most plastic materials have refractive indices of about 1.50. Those difficulties can be overcome by disposing an intermediate layer between the dielectric $SiO_2$ layer and the substrate, the refractive index of the intermediate layer differing from those of the silicon dioxide and the substrate and giving only a low degree of reflection for a given wavelength (in particular, 570 nm). The thickness of the two layers, namely the intermediate layer and the dielectric $SiO_2$ layer, depends on the refractive indices of the intermediate layer and the substrate.

As the front side of the plate, or the surface of the substrate on which the $SiO_2$ layer is disposed, is coated with an anti-reflection layer, reflection from the back of the substrate must be suppressed. That can be achieved by using a substrate which is slightly light-absorbent, for example, a dark-coloured glass or plastic. The colour in that substrate may be uniformly distributed in the substrate or may be contained within a coloured layer having the same refractive index as the remainder of the substrate. Particularly suitable are semiconductors which optically appear as absorbing dielectrics with high refractive indices, for example silicon.

In that way, immunological investigations may advantageously be carried out without using additional instruments, and inexpensive substances can be used for the detection members. The method and member according to the present invention provides detection in respect of thin organic layers, which can be visually ascertained by the naked eye. The detection members, which for example may be in the form of plates, can readily be reproduced using conventional methods, with a high degree of reproducibility. The detection members have a high degree of detection sensitivity, are easy to use, and can be inexpensively produced on an industrial scale, that is to say, by mass production.

When performing a visual detection operation, it is merely necessary for the detection member after it has been removed from the serum to be irradiated with white light on the side at which the array of layers is present, the white light being reflected there. Good contrast which is visible to the naked eye is attained when for example an antigen or antibody layer has been deposited on the layer of the detection reactant. Such contrast can be achieved with a high degree of uniformity and reproducibility. The chemically inert surface of the detection member does not affect the biochemical reactions, such as antigen-antibody reactions. The chemical properties of the correspondingly coated surface of the substrate facilitate the binding of different proteins. The detection member is physically rugged and has a long service life. In this way, immunological investigations can be carried out at extremely low cost, as no special equipment is required.

Advantageously, the dielectric used is silicon dioxide having the surface properties which are particularly suited to the purposes of the present invention, while the substrate may be an inert dielectric material. A further dielectric layer which in particular may comprise SiO will be arranged between the dielectric silicon dioxide layer and the substrate, in order to produce the desired optical properties. The substrate has a sufficient absorption capability and is of a dark appearance in transmission.

The method according to the principles of this invention therefore provides simplified optical detection of the substance to be detected, while the dielectric layers provide electrical insulation relative to the semiconducting substrate.

As the reaction between the substance to be detected and the detection or counter reactant takes place within a given part of the surface of the array of layers of the detection member, it is possible to obtain information relating to the level of concentration or the amount of the substance to be detected, in the test solution, in dependence on the geometrical dimensions of the reaction zone. It is also possible to determine the level of concentration or the amount of the substance to be detected, in dependence on the thickness of a gel member if for example it is applied to the array of layers, in a wedge-shaped cross-section, with the test solution having the substance to be detected contained therein being transported by diffusion through the gel member towards the top layer of detection reactant.

The invention may thus be used with advantage in detecting those biochemical substances which form one of the reactants in a biospecific, biomolecular reaction, for example in antigen-antibody reactions, enzyme-substrate reactions or toxin-receptor reactions.

In accordance with the principles of this invention, it is possible to achieve a degree of detection sensitivity which is close to the theoretical optimum. The high level of sensitivity is achieved by virtue of the combination of the strong interference effect and the strong optical coupling or incorporation of the biolayer into the interference phenomenon. The latter may only be achieved at a relatively low level of reflection. Metals are at a disadvantage in this respect, in comparison with dielectric layers which are employed in accordance with this invention.

The chemical properties of the silicon dioxide surface are versatile but can be accurately determined. Therefore, a wide range of organic molecules can be bound as a detection reactant to the $SiO_2$ surface by adsorption or covalent binding, using organo-silicon compounds as the coupling agent. For example, the $SiO_2$ surface may be made highly hydrophobic by treatment with dichlorodimethylsilane. That results in a surface which has a strong adsorption effect on many protein molecules.

The detection bodies used in accordance with the present invention are chemically inert and can be cleaned and regenerated by means of oxidising acids. There is no danger of metal ions being given off during a prolonged incubation period, which would result in contamination of the organic substances.

The detection members may be produced in plate form on an industrial scale. The dielectric layers can preferably be produced by vapour deposit or spraying. Such methods are simpler and can be carried out with a higher degree of accuracy than the anodization or vapour deposit of granular metal layers or the thermal oxidation of metal alloys. The optical requirements in respect of the detection members according to the invention are extremely low and the dimensions of the detection members may be determined in dependence on the requirements involved.

PREFERRED EMBODIMENTS OF THE INVENTION

Example 1

Silicon monoxide is evaporated on to a silicon wafer. The surface layer of the silicon monoxide if oxidized to form silicon dioxide, by the ambient air. The thickness of the layer of $SiO_2$ is from 2 to 3 nm, and the thickness of the layer of $SiO$ is from 60 to 70 nm.

That procedure provided a starting member for forming the definitive detection member according to the invention.

Example 2

Silicon monoxide is evaporated on to a dark-coloured glass slide or plate, in a thickness of from 60 to 70 nm. Oxygen gas is then introduced into the evaporation chamber and silicon monoxide continues to be evaporated and in the presence of the oxygen gas it becomes silicon dioxide, which is deposited on the silicon monoxide in the presence of the oxygen gas, and the evaporation process is stopped as soon as the $SiO_2$ layer reaches a thickness of from 90 to 100 nm.

The $SiO_2$ layers on both members described in Example 1 and in Example 2 are somewhat thinner than is required for optimum suppression of the reflected light. Restricted island areas in the surface of the $SiO_2$ layer are coated with monomolecular layers comprising proteins or antibodies. The remaining parts of the surface of the respective $SiO_2$ layer are coated with proteins which are different therefrom, so that the entire surface of the dielectric is covered by an optically uniform coating. The $SiO_2$ layers are each somewhat thinner than is required for optimum suppression of the reflected light, as referred to above, and the uniform organic layers applied thereto were of such a nature and size that the reflection is close to the reflection minimum.

The plates were then introduced into a solution containing organic molecules which react with the organic layers in the above-mentioned limited island areas in the surfaces thereof. The binding of molecules to those active island surface areas causes an increase in thickness of from 1 to 5 nm, depending on the substances used. The plates are removed from the solution, and dried. It is then found that the island areas are clearly visible to the naked eye and are somewhat darker and more purple than the surrounding surface when white light is reflected. Levels of concentration of down to 1 ng/ml solution can be easily detected in that way.

Reference will now also be made to the accompanying drawings which show diagrammatic views of embodiments of the detection member in accordance with the teaching of this invention.

DETAILED DESCRIPTION OF THE DRAWINGS

Figure 1:
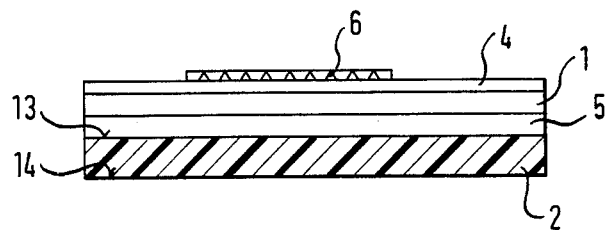
FIG. 1 shows a first embodiment of a detection member.
Figure 2:
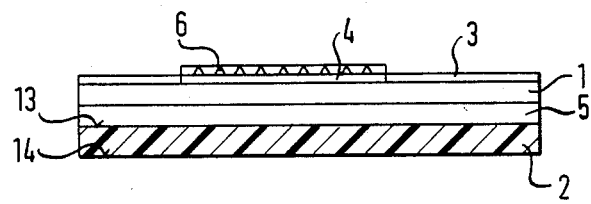
FIG. 2 shows a second embodiment of the detection member.

Referring firstly to FIGS. 1 and 2, the detection member or layer member comprises a carrier wafer or substrate 2 in the form of a plate and a dielectric layer 1 comprising $SiO_2$. The dielectric layer 1 is coated with a layer 4 of detection reactant or counter reactant. The layer 4 is capable of reacting with the substance to be detected, for example as a biomolecular reaction, more specifically an enzyme-carrier reaction, a toxin-receptor reaction, an antigen-antibody reaction, or the like. In performing the detection method, a layer 6 of the substance to be detected, for example comprising the corresponding antibody or antigen, is formed on the layer 4, for example by binding thereon.

Interposed between the substrate 2 and the layer 1 is at least one further dielectric layer, as indicated at 5, to which more detailed reference will be made below, after briefly describing the basic structure of the configuration shown in FIG. 2.

Referring now therefore to FIG. 2, in the embodiment of the detection member illustrated therein, the layer 4 of detection reactant is formed by a restricted area constituting a spot or island, surrounded by a non-active organic layer 3 which is of the same optical properties as the layer 4. The layers 3 and 4 are applied in monomolecular form.

Referring now to both FIGS. 1 and 2, having described the basic structure of the member in regard to the substrate 2 and the layer 1, interposed between the dielectric layer 1 and the substrate 2 is at least one further dielectric layer 5 which, in the illustrated constructions, comprises $SiO$. It will be appreciated that it is also possible to provide a plurality of further dielectric layers 5 between the layer 1 and the substrate 2. The thicknesses of the individual layers 1, 3, 4 and 5 are such that, when an additional layer in the form of the layer 6 of substance to be detected is deposited on the layer 4 in monomolecular form, for example by a binding action, the overall array of layers causes a change in colour in the region of the layer 6 of substance to be detected. That change in colour is preferably in the wavelength range to which the eye is most sensitive. At the same time, it is possible for the outermost surface layer to be of such a nature that it has the desired chemical and physical properties for the detection reaction.

The substrate 2 used may comprise for example glass, silicon or plastic material. The material forming the substrate 2 is such that it has a light-absorbing action. Absorption of light may take place over the entire substrate, or within a given layer on the substrate. That ensures that no light is reflected at the rear surface 14 of the substrate 2, but only at the surface 13 of the substrate on which the array of layers is formed.

Figure 3:
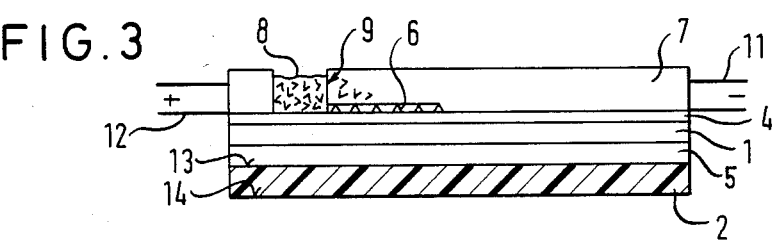
FIGS. 3 through 5 show further embodiments in regard to transportation of the substance to be detected, through a gel member, by means of electrophoresis or diffusion.
Figure 4:
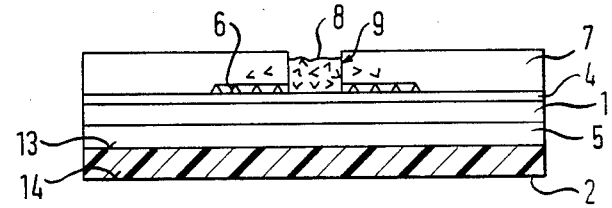
Figure 5:
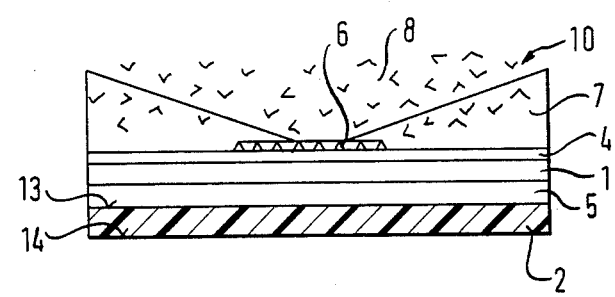

Reference will now be made to FIGS. 3 through 5 showing embodiments in which the substance to be detected is transported through a gel member which is applied to the layer 4 of detection reactant.

Referring firstly and more specifically therefore to Figure 3, formed in the gel body 7 is a recess 9 which constitutes a container means and which is filled with a test solution 8 containing the substance to be detected. That substance is transported through the gel body 7 along the surface of the layer 4, by means of an electrophoresis process in which an electrical field is produced in the gel body 7 by electrodes indicated at 11 and 12. The direction of transportation of the substance to be detected through the gel body 7 depends on the direction of the electrostatic field applied to the gel body 7.

In the embodiment illustrated in FIG. 4, the gel body 7 has one or more recesses 9 constituting containers for the test solution. The substance to be detected is transported by diffusion in a radial direction, from the test solution 8 in the recess 9. The transportation effect takes place along the surface of the layer 4.

In the embodiment shown in FIG. 5, the gel body 7 is applied to the layer 4, in such a way as to constitute a wedge-shaped configuration as can be clearly seen from FIG. 5. The test solution 8 with the substance to be detected is disposed above the gel body 7 with its wedge-shaped cross-section. The substance to be detected is transported in the gel body 7 substantially perpendicularly to the surface of the layer 4.

In that case, the substance to be detected first reacts at the location at which the gel body 7 is at its thinnest. In the course of time, a reaction also occurs between the substance to be detected and the layer 4, at the locations at which the gel body 7 is thicker. The reason for that is that the detection limit depends on the thickness of the gel body 7. Therefore, if the detection reaction is carried out within a certain period of time, it is possible to determine the concentration or the amount of the substance to be detected, in the test solution 8. The geometrical dimension of the reaction zone within which the substance to be detected occurs in the form of a layer 6 on the layer 4 of detection reactant constitutes a measurement in respect of the level of concentration or amount of the substance to be detected in the solution.

The amount of substance to be detected in the solution can be ascertained by means of standard curves which were obtained by measuring known test solutions, by measuring the size of the reaction zones. This procedure therefore readily permits quantitative detection of the amount of substance to be detected in the solution.

It will be seen therefore that the above-described method and member according to the present invention combines a high degree of sensitivity and good chemical properties, with easy production of the detection members in large numbers. The novel detection member described and illustrated herein is physically rugged and can be produced by standard industrial procedures, with a high degree of reproducibility and reliability, combined with versatile chemical properties of the surface of the member. The detection member can also readily provide a long shelf life and low manufacturing cost in relation to the total cost of the tests to be performed.

It will also be appreciated that various modifications and alterations may be made in the above-described method and detection member, without thereby departing from the spirit and scope of the present invention, for example the refractive index of the substrate 2 may be from 1.45 to 1.90, with the further or intermediate dielectric layer or layers 5 having a different refractive index from the substrate 2 and the first-mentioned dielectric layer 1.

We claim:

1. A member for detection of a chemical substance in a medium, comprising: a non-metal substrate having a surface; a first dielectric $SiO_2$ layer overlying said substrate; a detection reactant on the first dielectric layer and capable of reacting with the substance to be detected such that an optically detectable layer of the substance to be detected is formed on the detection reactant upon the introduction of said member into a medium to be investigated; and at least one further dielectric layer between said surface of said substrate and the first dielectric layer and of such a thickness and with such a refractive index that in operation of the member having an overall layer array including the first and further dielectric layers, the detection reactant and thereon the layer of substance to be detected, the overall layer array operates to reduce reflection in respect of non-monochromatic light which is reflected at said surface of the substrate, in the wavelength range of from 525 to 600 nm.

2. A member as set forth in claim 1 wherein said detection reactant is provided on only a part of said first dielectric layer.

3. A member as set forth in claim 2 wherein said detection reactant is provided at a plurality of mutually separated locations on said first dielectric layer.

4. A member as set forth in claim 2 wherein said detection reactant is provided in an island configuration on said first dielectric layer and the island portion of detection reactant is surrounded by a layer of non-active organic substance of the same thickness and optical properties as said detection reactant.

5. A member as set forth in claim 1 wherein said first dielectric layer is treated with an organo-silicon compound to bind the detection reactant thereto.

6. A member as set forth in claim 1 wherein said detection reactant is an antigen.

7. A member as set forth in claim 1 wherein said detection reactant is an antibody.

8. A member as set forth in claim 1 wherein said detection reactant is applied to said first dielectric layer in a layer in monomolecular form.

9. A member as set forth in claim 1 wherein said substrate is light-absorbing.

10. A member as set forth in claim 1 wherein said at least one further dielectric layer has a different refractive index from said substrate and said first dielectric layer.

11. A member as set forth in claim 1 wherein said at least one further dielectric layer comprises $SiO$.

12. A member as set forth in claim 1 wherein said substrate has a refractive index of from about 1.45 to 1.90.

13. A member as set forth in claim 1 wherein said substrate comprises dark-coloured glass.

14. A member as set forth in claim 1 wherein said substrate comprises dark-coloured plastic material.

15. A member as set forth in claim 1 wherein said substrate comprises silicon.

16. A member as set forth in claim 1 which is in the form of a plate.

17. A member as set forth in claim 1 and including a layer of gel substance on said detection reactant layer.

18. A member as set forth in claim 17 wherein said gel layer is of a wedge-like cross-sectional configuration.

19. A method of detecting a biochemically reactive substance in a medium comprising: providing a detection member which includes a substrate having a surface, depositing on said surface at least one dielectric layer, depositing on said at least one dielectric layer a dielectric layer of $SiO_2$, and depositing on said $SiO_2$ layer a layer of a detection reactant capable of reacting with the substance to be detected such that a visually discernible layer of said substance is formed on the detection reactant, the thickness and the refractive index of said at least one dielectric layer being such that the overall layer array comprising said at least one dielectric layer, said $SiO_2$ layer, said detection reactant layer and said layer of said substance formed thereon is at least substantially reflection-reducing in respect of non-monochromatic light which is reflected at said substrate surface in a wavelength range of 525 to 600 nm; bringing said detection member into contact with said substance to be detected in said medium whereby said visually discernible layer is formed on said member; and irradiating said detection member with non-monochromatic light to cause same to be reflected with reduced reflection at said substrate surface, thereby producing a visually discernible change in colour on at least part of said detection member bearing said layer of substance to be detected, relative to at least another part of said member, which is without said substance.

20. A method as set forth in claim 19 wherein said detection member has gel on its said $SiO_2$ layer and wherein said substance to be detected is caused to react with the layer of detection reactant by transportation in the gel on said $SiO_2$ layer relative to the layer of detection reactant, and the gel is removed for the visual observation step.

21. A method as set forth in claim 20 wherein said transportation is by diffusion effect.

22. A method as set forth in claim 20 wherein said transportation is by electrophoresis.

23. A method as set forth in claim 19 wherein the geometrical extent of the region of the detection member in which the substance to be detected is formed as a layer thereon is a measurement in respect of the concentration thereof.

24. A method as set forth in claim 19 wherein the geometrical extent of the region of the detection member in which the substance to be detected is formed as a layer thereon is a measurement in respect of the amount thereof.

25. A method as set forth in claim 20 wherein said gel has at least one recess therein for receiving a test solution containing the substance to be detected, and wherein said test solution is introduced into said at least one recess in the gel, said test solution being transported in a radial direction out of said at least one recess into the gel body.

26. A method as set forth in claim 20 wherein said gel is applied to said detection member in different thicknesses and the amount of the substance to be detected is determined from at least one of the factors comprising the position and the geometrical dimensions of the surface region on the detection member in which said change in colour takes place after a given reaction time.

27. A method as set forth in claim 26 wherein said gel is applied to said detection member in a wedge-shaped cross-sectional configuration thereon.

28. A member as set forth in claim 1 wherein said substrate and said further dielectric layer define a base for said $SiO_2$ layer, said base having a refractive index of about 2.13.

* * * * *